US010953182B2

(12) United States Patent
Zhan et al.

(10) Patent No.: US 10,953,182 B2
(45) Date of Patent: Mar. 23, 2021

(54) BREATHING MASK

(71) Applicant: BMC MEDICAL CO., LTD., Beijing (CN)

(72) Inventors: Yifeng Zhan, Beijing (CN); Zhi Zhuang, Beijing (CN)

(73) Assignee: BMC MEDICAL CO., LTD., Beijing (CN)

(*) Notice: Subject to any disclaimer, the term of this patent is extended or adjusted under 35 U.S.C. 154(b) by 184 days.

(21) Appl. No.: 15/742,298

(22) PCT Filed: Dec. 29, 2016

(86) PCT No.: PCT/CN2016/112947
§ 371 (c)(1),
(2) Date: May 10, 2018

(87) PCT Pub. No.: WO2017/114454
PCT Pub. Date: Jul. 6, 2017

(65) Prior Publication Data
US 2018/0250485 A1    Sep. 6, 2018

(30) Foreign Application Priority Data

Dec. 31, 2015   (CN) .......................... 201511026812.4
Dec. 31, 2015   (CN) .......................... 201511029467.X

(51) Int. Cl.
*A61M 16/06*    (2006.01)
*A61M 16/08*    (2006.01)

(52) U.S. Cl.
CPC .......... *A61M 16/065* (2014.02); *A61M 16/06* (2013.01); *A61M 16/0638* (2014.02);
(Continued)

(58) Field of Classification Search
CPC ....... A62B 9/00; A62B 9/02–027; A62B 7/00; A62B 7/04; A62B 7/14; A61M 16/00;
(Continued)

(56) References Cited

U.S. PATENT DOCUMENTS 2,245,658 A * 6/1941 Erickson ........... A61M 16/0633
                                                           128/206.28
2004/0177850 A1   9/2004 Gradon et al.
(Continued)

FOREIGN PATENT DOCUMENTS

CN          101115521 A       1/2008
CN          102019022 A       4/2011
(Continued)

*Primary Examiner* — Timothy A Stanis
*Assistant Examiner* — Ned T Heffner
(74) *Attorney, Agent, or Firm* — Volpe Koenig

(57) ABSTRACT

A breathing mask comprises: a frame; a forehead support frame connected to the frame pivotally to allow the forehead support frame to shift toward or away from the forehead of a patient; and an adjusting member connected to the frame rotatably and having an adjusting slope. The forehead support frame has a joining part in contact with the adjusting slope so that the forehead support frame is driven to rotate pivotally through the rotation of the adjusting member. Through the matching between the adjusting slope and the joining part, the breathing mask converts the rotation of the adjusting member to the shifting of the forehead support frame; and through rotating the adjusting member, the height of the forehead support frame relative to the forehead of the patient can be adjusted. In use, the forehead support frame can be shifted by rotating the adjusting member with a single hand.

8 Claims, 10 Drawing Sheets

(52) U.S. Cl.
CPC ..... *A61M 16/0655* (2014.02); *A61M 16/0622* (2014.02); *A61M 16/0825* (2014.02)

(58) Field of Classification Search
CPC ........... A61M 16/06–0694; A61M 16/20–209; A61M 16/0003–0012; A61M 2016/0015–0042; B63C 11/12; B63C 11/18
See application file for complete search history.

(56) References Cited

U.S. PATENT DOCUMENTS

| | | | |
|---|---|---|---|
| 2007/0044804 A1* | 3/2007 | Matula, Jr. ............ | A61M 16/06 128/206.21 |
| 2010/0108069 A1* | 5/2010 | Chang .................... | A61M 16/06 128/205.25 |
| 2011/0126838 A1 | 6/2011 | Alberici et al. | |
| 2014/0000617 A1 | 1/2014 | Rothermel et al. | |
| 2015/0136133 A1 | 5/2015 | Berthon-Jones | |
| 2015/0367095 A1 | 12/2015 | Lang et al. | |

FOREIGN PATENT DOCUMENTS

| | | |
|---|---|---|
| CN | 102781505 A | 11/2012 |
| CN | 103182126 A | 7/2013 |
| CN | 104906676 A | 9/2015 |
| CN | 105079933 A | 11/2015 |
| CN | 105413036 A | 3/2016 |
| CN | 105413037 A | 3/2016 |
| CN | 205268790 U | 6/2016 |
| CN | 205287177 U | 6/2016 |
| DE | 102009051781 A1 | 5/2011 |
| TW | M322820 U | 12/2007 |
| WO | 2011107899 A1 | 9/2011 |
| WO | 2013098694 A1 | 7/2013 |
| WO | 2014009838 A1 | 1/2014 |

* cited by examiner

BREATHING MASK

CROSS REFERENCE TO RELATED APPLICATION

This application is a 35 USC § 371 National Stage application of International Patent Application No. PCT/CN2016/112947, which was filed Dec. 29, 2016 and claims priority to Chinese Application No. 201511029467.X, filed on Dec. 31, 2015 and entitled "Breathing Mask," and Chinese Application No. 201511026812.4, which was filed on Dec. 31, 2015 and entitled "Breathing Mask," all of which are incorporated herein by reference as if fully set forth.

FIELD OF THE INVENTION

The present application relates to the technical field of breathing masks, in particular to a breathing mask.

BACKGROUND OF THE INVENTION

At present, obstructive sleep apnea hypopnea syndrome (OSAHS) is mainly treated by applying continuous positive airway pressure (CPAP). However, utilizing CPAP, usually the patient has to wear a breathing mask for a long time (e.g., overnight). Therefore, the wearing comfortability has great influence on the experience of the patient. If the patient feels the comfortability is unsatisfactory when wearing the breathing mask, the patient may reject the treatment or adjust the position of the breathing mask frequently. Especially during the night time, the patient may touch the breathing mask unconsciously. Such an action may result in gas leakage from the breathing mask and thereby affects the treatment result.

Most existing breathing masks are equipped with a forehead support frame. The forehead support frame abuts against the forehead of the patient, so that a sense of pressure exerted by the breathing mask on the face can be mitigated utilizing the supporting force provided by the forehead. However, the height of forehead may be different among different patients, depending on race, age, and individual person. The foreheads 100 plotted in a solid line and a dotted line in FIG. 1 show the difference in forehead height respectively. Therefore, the breathing mask should be supported at an appropriate height on the forehead to ensure an optimal wearing sense and provide a comfortable wearing experience to the patient.

At present, the height of the forehead support frame in relation to forehead is adjusted utilizing a screw-drive principle; specifically, a forehead support pad on the forehead support frame is driven to extend or retract by means of rotation movement of a knob, so as to adapt to specific forehead height. However, such an adjusting mechanism involves a large number of parts and components, and is difficult to implement; in addition, such an adjusting mechanism involves high requirements for the manufacturing process, and results in a high manufacture cost.

CONTENTS OF THE INVENTION

To at least partially solve the problems of complex structure and high manufacture cost of existing breathing masks, the present application provides a breathing mask, which improves convenience of forehead support member adjustment.

According to an aspect of the present application, the present invention provides a breathing mask, which comprises: a frame; a forehead support member, which is pivotally connected to the frame to allow the forehead support member to swing toward the forehead of a patient or swing away from the forehead of the patient; and an adjusting member, which is rotatably connected to the frame, wherein, the forehead support member is driven to swing by means of the rotation of the adjusting member. The breathing mask provided in the present application comprises an adjusting member rotatably connected to the frame, and the height of the forehead support member in relation to the forehead of the patient can be adjusted by rotating the adjusting member. During use, the forehead support member may be driven to swing by rotating the adjusting member with a single hand, and the patient can find out the most comfortable position according to his/her feeling, without any help from any other person. Hence, the operation is very convenient. In addition, such an adjusting method involves a simple structure and a very small number of parts and components. Therefore, the manufacturing process is simple, and the manufacture cost is low.

The concepts of a series of simplified forms are introduced in this section, and will be further detailed in the detailed description of the embodiments. The content of the present application is not intended to define key features and essential technical features of the technical scheme claimed for protection or intended to define the protection scope of the technical scheme claimed for protection.

Here under the advantages and features of the present application will be detailed with reference to the accompanying drawings.

DESCRIPTION OF THE DRAWINGS

The following drawings are presented here as a part of the present application to facilitate the understanding on the present application. The drawings show embodiments and provide description of the present application to interpret the principle of the present application. In the drawings.

DETAILED DESCRIPTION OF THE EMBODIMENTS

In the following description, many details are provided to facilitate thorough understanding on the present application. However, those skilled in the art should appreciate that the following description only exemplarily describes some preferred embodiments of the present application, and the present application can be implemented without one or more of such details. Besides, to avoid confusion with the present application, some technical features that are well known in the art are not detailed here.

Figure 1:
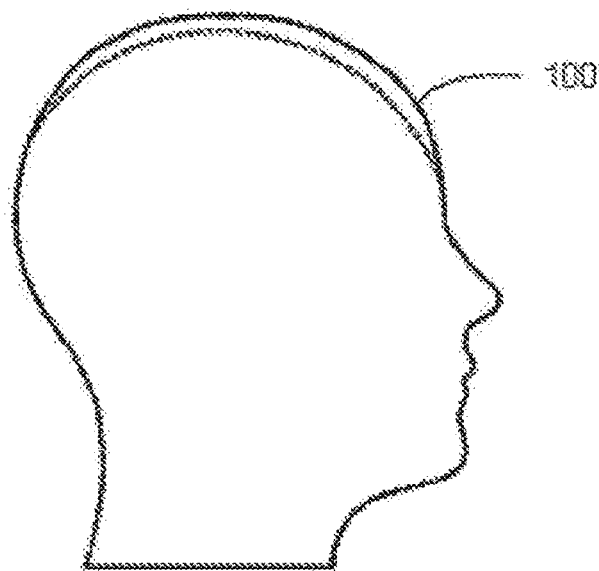
FIG. 1 is a schematic diagram of the profile of a human head.
Figure 2:
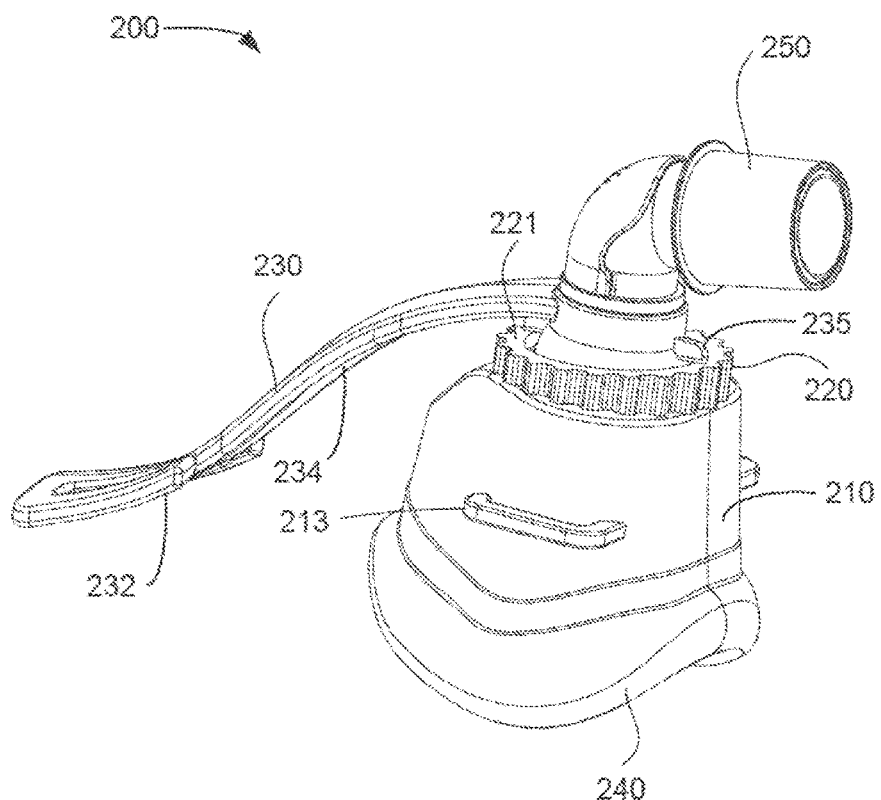
FIG. 2 is a 3D view of the breathing mask according to an embodiment of the present application.
Figure 3:
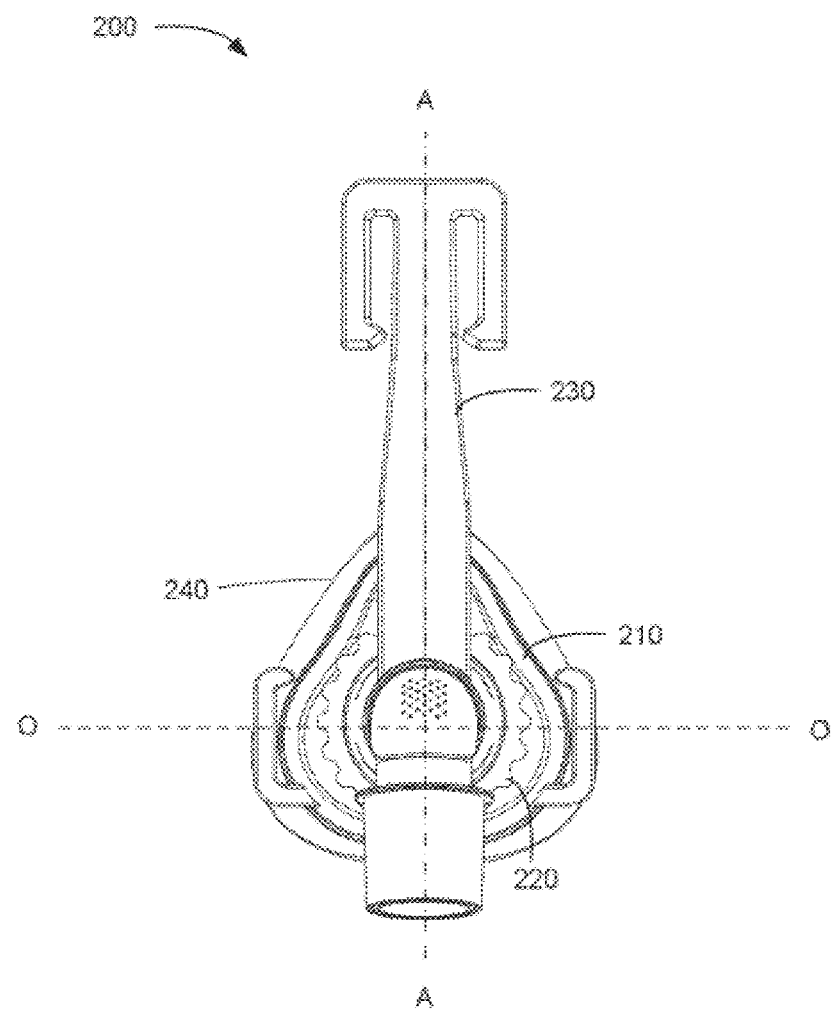
FIG. 3 is a front view of the breathing mask in FIG. 2.
Figure 4:
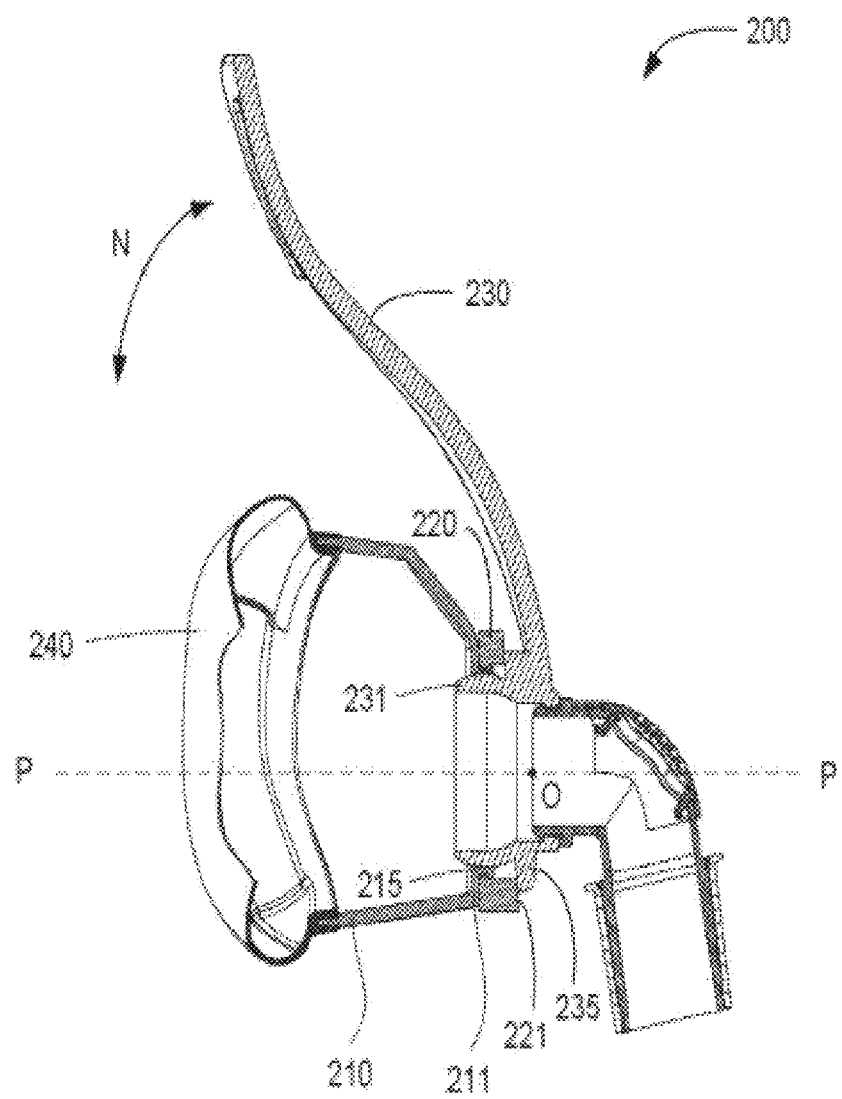
FIG. 4 is a sectional view A-A of the breathing mask in FIG. 3.

According to an aspect of the present application, the present invention provides a breathing mask. FIGS. 2-4 show the breathing mask 200 according to an embodiment of the present application from different angles, wherein, FIG. 2 is a 3D view of the breathing mask according to an embodiment of the present application; FIG. 3 is a front view of the breathing mask in FIG. 2; FIG. 4 is a sectional view A-A of the breathing mask in FIG. 3. It should be understood: though the principle of the present application is described exemplarily with a nasal breathing mask shown in the accompanying drawings, alternatively the breathing mask provided here may be an oral-nasal breathing mask, a full-face breathing mask, or a nasal pillow type breathing mask, etc. As shown in FIGS. 2-4, the breathing mask 200 may comprise a frame (also referred to as main body of mask) 210, an adjusting member 220, and a forehead support member 230.

The frame 210 is mainly used to support the entire breathing mask 200. The frame 210 may be fixedly or removably connected with a cushion 240. The cushion 240 and the frame 210 jointly form a cavity for accommodating the nose part or nose and mouth part of the patient. Alternatively, the cushion 240 may solely form the cavity. In this embodiment, the frame 210 may support the cushion 240 outside of the cushion 240. During use, the cushion 240 contacts with the face (including cheeks, nose bridge, and upper part or bottom part of mouth, etc.) to form an enclosed space, so that the cavity communicates with the nasal cavity or oral and nasal cavities of the patient. The frame 210 may be made of a rigid material or flexible material. The cushion 240 preferably is made of a flexible material. The rigid material may be plastics or alloy, etc.; the flexible material may be silica gel, gel, foam, air bag, or textile, etc., for example. View from the side opposite to the patient after the breathing mask 200 is worn by the patient, the shape of the frame 210 and cushion 240 is not limited to a general triangle as shown in the drawings, and may be a pear shape or trapezoid shape, etc. The frame 210 and the cushion 240 may be in any other shape that matches the shape of the mouth and/or nose. The frame 210 may be provided with a gas transfer interface 211, via which breathable gas is supplied to the cavity in the breathing mask 200. The gas transfer interface 211 has a central axis P-P that extends in the gas flow direction. Besides, the frame 210 may be provided with a fixing structure 213 configured to connect a fixed assembly (not shown in FIG. 2). The fixing structure 213 is used to fix the breathing mask 200 to an appropriate position on the face of the patient, and may be any headgear in the prior art. The headgear may have a structure for connecting to the frame 210, such as a buckle or a strap with a hook & loop fastener.

During use, the forehead support member 230 abuts against the forehead of the patient to fix the breathing mask 200 to the face of the patient more firmly and comfortably. The forehead support member 230 is pivotally connected to the frame 210, to allow the forehead support member 230 to swing toward the forehead of the patient or swing away from the forehead of the patient. As an example, the forehead support member 230 may be pivoted around a pivot shaft O-O, which serves as an axis. In the nasal breathing mask, preferably, the forehead support member 230 is pivotally (i.e., shiftably) connected to the gas transfer interface 211, so that the structure of the breathing mask is more compact. However, for a breathing mask in a larger size (e.g., full-face mask or oral-nasal mask, etc.), the forehead support member 230 may be arranged on the frame 210 separately from the gas transfer interface 211. The pivot shaft O-O extends in left-right direction of the human body. When the forehead support member 230 is pivoted around the pivot shaft O-O (in the direction indicated by the arrow N in FIG. 4), the height of the forehead support member 230 in relation to the forehead may be adjusted. The connection between the forehead support member 230 and the frame 210 may be non-detachable or detachable. The forehead support member 230 has a first connecting part 231. The forehead support member 230 is connected to the frame 210 via the first connecting part 231. The forehead support member 230 may further comprise a connecting arm 234 and a forehead support pad 232. The connecting arm 234 extends from the first connecting part 231 along the nose bridge essentially to the vicinity of the forehead. The soft forehead support pad 232 is arranged at the end of the connecting arm 234 near the forehead and is configured to abut against the forehead of the patient. Adjusting the height of the forehead support member 230 actually is adjusting the height of the forehead support pad 232 in relation to the forehead.

The pivotal connection between the forehead support member 230 and the frame 210 may be implemented in a variety of ways. In a preferred embodiment, the forehead support member 230 has a first connecting part 231. The frame 210 has a second connecting part 215. The first connecting part 231 and the second connecting part 215 are fitted with each other to form a ball and socket connection structure. In a preferred embodiment, the first connecting part 231 is in a truncated sphere shape, and is pivotally received in the second connecting part 215. A truncated sphere refers to a part of a sphere between two parallel planes when the sphere is truncated by the two parallel planes. Of course, alternatively the second connecting part 215 may be designed to be received in the first connecting part 231. However, compared with the preferred design shown in the drawings, the design in which the second connecting part 215 is received in the first connecting part 231 involves the following problems: The second connecting part 215 inside the first connecting part 231 has to be designed longer so as to leave an adequate pivoting space for the first connecting part 231 outside the second connecting part 215; in addition, the first connecting part 231 doesn't take full advantage of the space in the cavity; consequently, the entire breathing mask 200 is bigger, causing degraded wearing comfortability. The spherical fitting between the first connecting part 231 and the second connecting part 215 may be interference fitting, to ensure gas tightness of the connection between the two parts.

Figure 6:
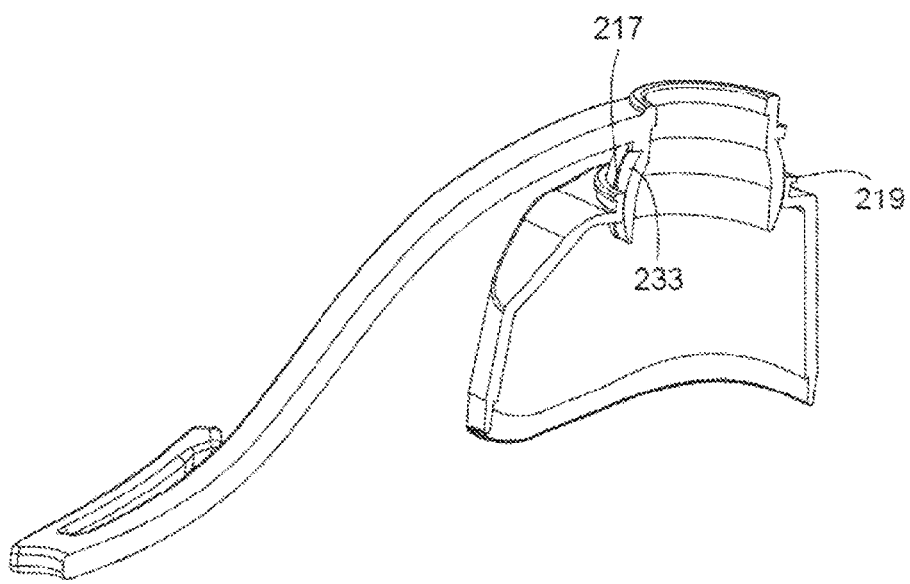
FIG. 6 is a sectional view of the breathing mask in FIG. 2 after a elbow assembly and an adjusting member are removed.

In the case of a ball and socket connection, to limit the swing direction of the forehead support member 230 (e.g., forcing the forehead support member 230 to pivot around the pivot shaft O-O, which serves as an axis), the forehead support member 230 and the frame 210 are respectively provided with a limit part, and the limit parts are fitted with each other. FIG. 6 is a sectional view of the breathing mask in FIG. 2, after an elbow assembly and an adjusting member are removed. Compared with FIGS. 2-4, in FIG. 6, the adjusting member 220 and the elbow assembly 250 are removed, and a limit part 233 (a limit slot) on the forehead support member 230 and a limit part 217 (a limit block) on the frame 210 are exposed. The limit block 217 slides along the limit slot 233 when the forehead support member 230 is swung. The limit parts may be implemented in other ways, for example, a limit block arranged on the forehead support member 230 and a limit slot arranged on the frame 210, which are fitted with each other; or flat faces that are fitted with each other (the flat faces may be perpendicular to the pivot shaft O-O), etc. With the limit parts, though the forehead support member 230 and the frame 210 are connected via a ball and socket connection, there is only the degree of freedom of adjustment in the height direction of forehead. Besides the above-mentioned ball and socket connection structure, the forehead support member 230 may be pivotally connected to the frame 210 via a hinge, alternatively. As an example, a hinge may be arranged on an external surface of the frame 210, and the forehead support member 230 is connected to the frame 210 via the hinge. However, compared with the above-mentioned preferred connection, such a hinge connection structure is more complex and difficult to disassemble and clean, and may cause the whole appearance of the breathing mask 200 is non-flat.

The breathing mask 200 may further comprise a elbow assembly 250. The elbow assembly 250 communicates with the gas transfer interface. A pressure sustaining apparatus (e.g., an respirator) is connected via a gas transfer tube (not shown) to the elbow assembly 250, so as to supply gas at appropriate pressure into the cavity of the breathing mask 200 and then into the airway of the patient. The gas supplied to the patient may be any appropriate respiratory gas known in the prior art. The elbow assembly 250 may be any elbow assembly commonly used in the art. The gas transfer tube may be a corrugated hose commonly used in the art. For the preferred embodiment shown in FIGS. 2-4, the forehead support member 230 is connected to the gas transfer interface 211, and the adjusting member 220 may also be connected to the gas transfer interface 211. A gas flow passage that allows the gas to flow through the gas transfer interface 211 is arranged in the first connecting part 231 of the forehead support member 230. The elbow assembly 250 may be connected to the first connecting part 231 of the forehead support member 230, and communicate with the gas flow passage in the first connecting part 231. In an embodiment in which the second connecting part 215 is received in the first connecting part 231, and in an embodiment in which the forehead support member 230 is connected to the frame 210 via a hinge, the elbow assembly 250 may be directly connected to the gas transfer interface 211.

It should be noted that the orientation terms involved in the present application, such as "front", "back", "upper", "lower", "left", "right", "inside", "outside", "distal", and "proximal", etc., are defined in relation to a patient who wears the breathing mask 200 with his/her head kept in an upright state. As for the placement shown in FIGS. 3-4, the cushion 240 is at the proximal end of the patient in relation to the elbow assembly 250, and the elbow assembly 250 is at the distal end of the patient in relation to the cushion 240.

Embodiment 1

In embodiment 1 of the present application, the breathing mask provided in the present application may comprise an adjusting member having an adjusting slope, and the rotation of the adjusting member is converted into the swing of a forehead support member by means of fitting between the adjusting slope and the joining part on the forehead support member; thus, the height of the forehead support member in relation to the forehead of the patient can be adjusted by rotating the adjusting member. Hereinafter the adjusting member 220 for adjusting the height of the forehead support pad in the embodiment 1 will be detailed. The adjusting member 220 is rotatably connected to the frame 210. Optionally, one of the adjusting member 220 and the frame 210 may be provided with a carrier, and the other of the adjusting member 220 and the frame 210 may be provided with a fitting component that can be moved along the carrier. Wherein, the above-mentioned carrier may comprise: a snap slot, which may form a snap-fit connection with the corresponding fitting component; or the above-mentioned carrier may comprise: a track, which may form a sliding connection with the corresponding fitting component.

Figure 5:
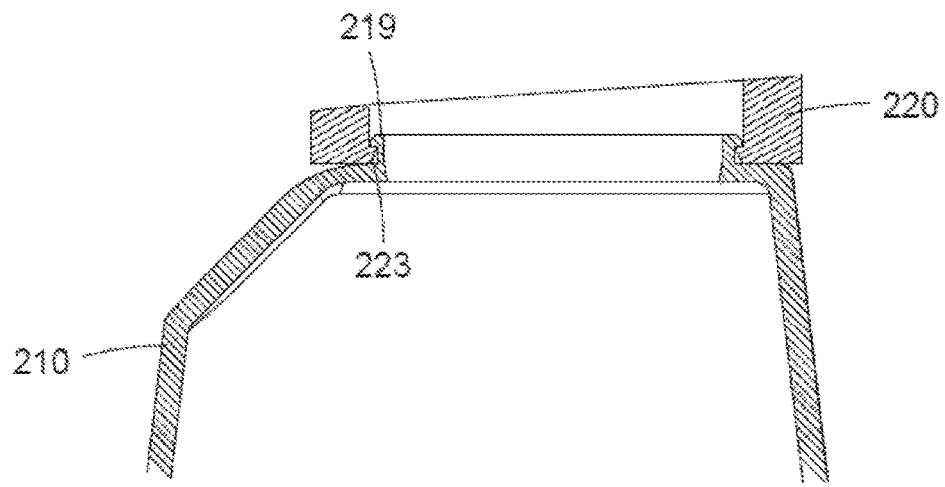
FIG. 5 is a partially enlarged view of the adjusting member in FIG. 4.

FIG. 5 is a partially enlarged view of the adjusting member in FIG. 4. In a preferred embodiment, as shown in FIG. 5, the adjusting member 220 is provided with a first snap slot 223, the frame 210 is provided with a second snap slot 219, and the first snap slot 223 and the second snap slot 219 may be snap-fitted with each other. The adjusting member is rotatably connected to the frame 210 via the first snap slot 223 and the second snap slot 219. The adjusting member 220 and the frame 210 may be rotated in relation to each other by means of rotation of the first snap slot 223 in relation to the second snap slot 219. As an example, at least one of the first snap slot 223 and the second snap slot 219 are in an annular shape, so that the one of the first snap slot 223 and the second snap slot 219 may be rotated in relation to the other of the first snap slot 223 and the second snap slot 219. In an embodiment in which the adjusting member 220 is connected to the gas transfer interface 211, the first snap slot 223 and/or the second snap slot 219 may extend in the circumferential direction of the gas transfer interface 211, so that the adjusting member 220 can be rotated around the gas transfer interface 211, which serves as an axis. At least one of the first snap slot 223 and the second snap slot 219 may be an annular slot arranged continuously in the circumferential direction of the gas transfer interface 211. Alternatively, the rotation of the adjusting member 220 and the frame 210 in relation to each other may be implemented with other fitting means. For example, one of the adjusting member 220 and the frame 210 may be provided with a circular track, and the other of the adjusting member 220 and the frame 210 may be provided with any fitting part that slides along the track, such as a protrusion, a clamping a hook, or teeth, etc.

The adjusting member 220 further has an adjusting slope. The adjusting slope is at an acute angle from a reference plane. The reference plane mentioned in the embodiments of the present application is a vertical plane parallel to the pivot shaft O-O. The reference plane is an imaginary plane, and is not shown in the drawings; however, with reference to FIG. 4, it can be understood that the reference plane is a vertical plane perpendicular to the paper surface. When a patient wears the breathing mask, the reference plane is parallel to the face of the patient. In FIG. 4, the adjusting slope may comprise a distal surface 221 away from the frame 210, and the distal surface 221 is a slope surface. The distal surface 221 and the reference plane form an acute angle. The forehead support member 230 has a joining part 235 that is contact with the adjusting slope (the distal surface 221 in this embodiment). Owing to the existence of the adjusting slope, the adjusting member 220 has thickness difference in a direction perpendicular to the face of the patient. Thus, the forehead support member 230 may be driven to swing by the rotation of the adjusting member 220, and thereby the height of the forehead support member 230 in relation to the forehead can be adjusted. When the adjusting member 220 is rotated after the patient wears the breathing mask 200, the adjusting slope of the adjusting member 220 will drive the joining part 235 on the forehead support member 230, and thereby drive the forehead support member 230 to swing in the direction indicated by the arrow N, so that the height of the forehead support member 230 is adjusted. Thus, the patient can find out the most comfortable position according to his/her feeling simply by rotating the adjusting member 220 with a single hand, without any help from any other person. The slope of the adjusting slope in relation to the reference plane may be designed according to the desired height adjustment range of the forehead support member 230. Thus it is seen: the adjusting member 220 is designed skillfully to implement height adjustment of the forehead support member 230, the structure and the manufacturing process is simple. Therefore, the cost can be saved.

In view that the adjusting slope includes only one slope surface (i.e., the distal surface 221) contact with the joining part 235 and each joining part 235 can form only one joining point, the forehead support member 230 may be designed to include a plurality of joining parts 235 to control the swing of the forehead support member 230. The plurality of joining parts 235 may be arranged as a plurality of protrusions on the forehead support member 230. As shown in FIG. 2, two protrusions are arranged opposite to each other on the forehead support member 230. The joining part 235 may include more protrusions.

Figure 7:
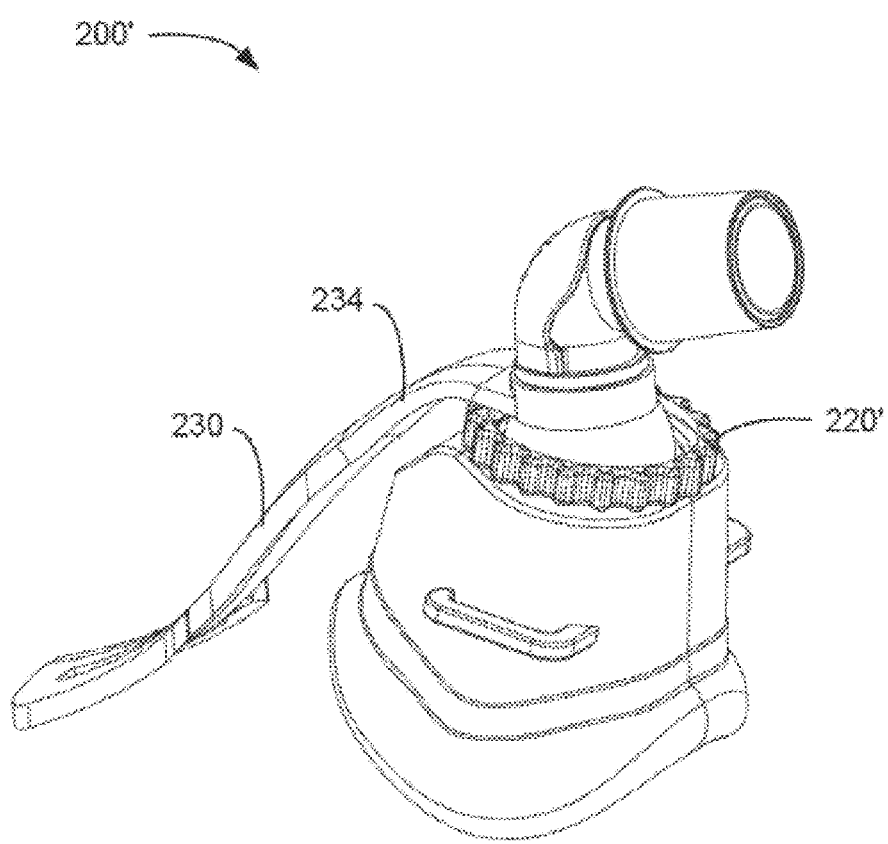
FIG. 7 is a 3D view of the breathing mask according to an embodiment of the present application.
Figure 8:
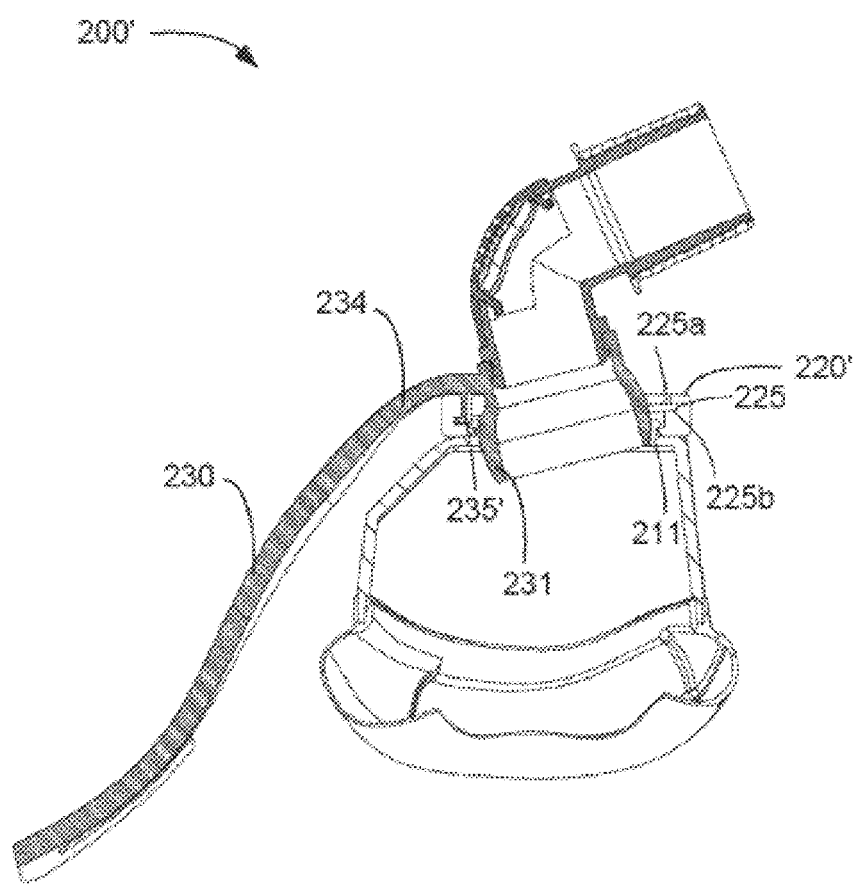
FIG. 8 is a sectional view of the breathing mask in FIG. 7.

Moreover, the present application further provides another preferred adjusting scheme with reference to FIGS. 7-8. FIG. 7 is a 3D view of the breathing mask according to an embodiment of the present application, and FIG. 8 is a sectional view of the breathing mask in FIG. 7. The breathing mask 200' shown in FIGS. 7-8 is essentially the same as the breathing mask 200 shown above, except for an adjusting member 220' and a joining part fitted with the adjusting member 220'. In FIGS. 7-8, the same or similar components are identified with symbols that are the same as those in the preceding embodiment. Hereunder only the differences will be detailed. As described previously, in a case that the adjusting slope includes only one slope surface, a plurality of joining parts must be arranged to control the swing of the forehead support member 230. In the preferred embodiment, the inner surface of the adjusting member 220' is provided with an annular slope slot 225. The annular slope slot 225 may be arranged on the side of the adjusting member 220' that faces the first connecting part 231 (i.e., the inner surface of the adjusting member 220'). The annular slope slot 225 surrounds the first connecting part 231. The annular slope slot 225 is arranged in a slope manner in relation to the above-mentioned reference plane. The annular slope slot 225 has a first side wall 225a and a second side wall 225b that are arranged opposite to each other. The space between the first side wall 225a and the second side wall 225b is the annular slope slot 225. Both the first side wall 225a and the second side wall 225b are at an acute angle from the reference plane mentioned above. The adjusting slope may comprise the first side wall 225a and the second side wall 225b. At least a part of a joining part 235' is arranged in the annular slope slot 225. The joining part 235' may slide along the annular slope slot. The joining part 235' contacts with the first side wall 225a and the second side wall 225b, and thereby the swing of the forehead support member 230 can be controlled with a single joining part 235'. Of course, alternatively a plurality of joining parts 235' may be arranged to share the acting force for controlling the swing of the forehead support member 230 to prolong the service life. The joining part 235' may be arranged at the inner side of the adjusting member 220', as shown in FIGS. 7-8, to ensure flat and smooth appearance of the breathing mask 200'. The joining part 235' may be arranged on a connecting arm 234, as shown in FIG. 8. Alternatively, the joining part 235' may be arranged on the first connecting part 231 or at any other appropriate position.

Figure 9:
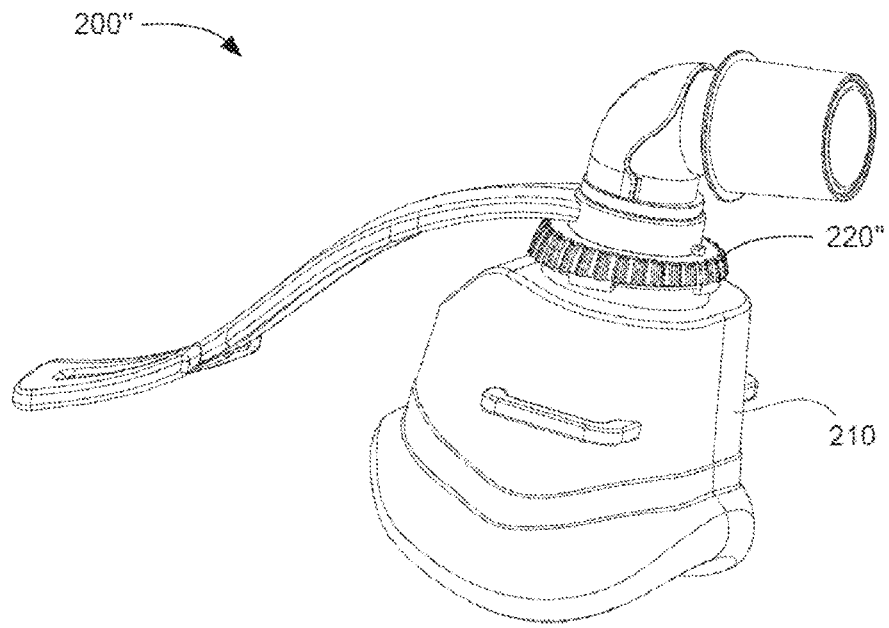
FIG. 9 is a 3D view of the breathing mask according to an embodiment of the present application.
Figure 10:
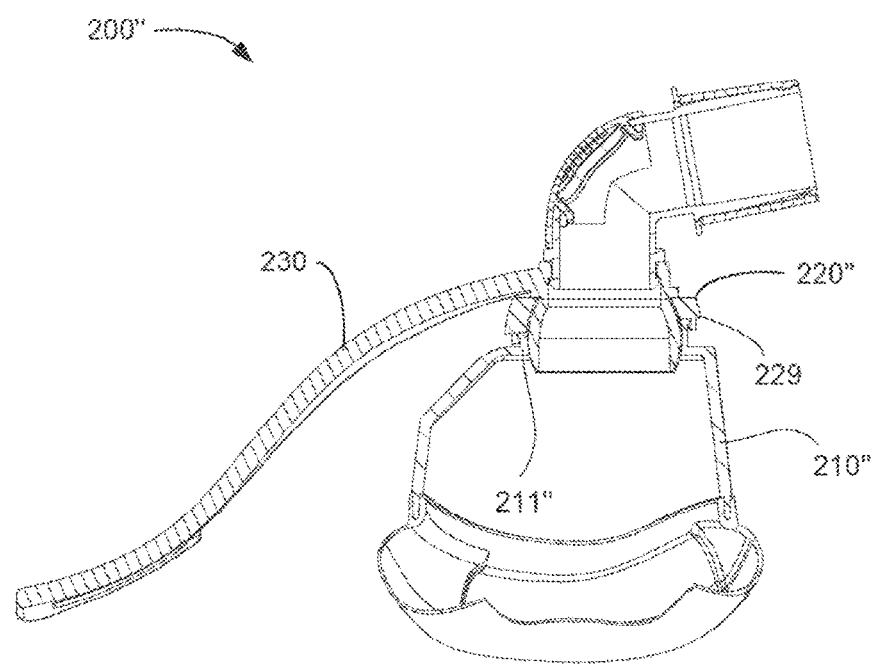
FIG. 10 is a sectional view of the breathing mask in FIG. 9.

In another group of embodiments, FIG. 9 shows a 3D view of the breathing mask according to an embodiment of the present application; FIG. 10 is a sectional view of the breathing mask in FIG. 9. As shown in FIGS. 9-10, the adjusting slope of the adjusting member 220" may include a proximal surface 229 that faces the frame 210, and the proximal surface 229 is a slope surface. The proximal surface 229 and the reference plane form an acute angle (a plane parallel to the face of the patient). Here, components of the breathing mask 200" that are the same as or similar to those of the above-mentioned breathing mask 200 and breathing mask 200' are identified with symbols that are the same as those in the preceding embodiments, and the detail description of the same or similar components is omitted. Hereunder only the differences will be mainly detailed. Furthermore, to fit with the proximal surface 229, the adjusting member 220" is also slope in relation to the rotation plane of the frame 210". The rotation plane is the plane where the adjusting member 220" lies when it is rotated, and the rotation plane and the reference plane form an acute angle. As an example, the end surface of the frame 210" that is contact with the proximal surface 229 is no longer made to be parallel to the reference plane, unlike a conventional component; instead, it is at an acute angle from the reference plane. The slope angle of the above-mentioned end surface of the frame 210" doesn't have to be the same as the slope angle of the proximal surface 229. Optionally, the above-mentioned end surface of the frame 210" may be parallel to the reference plane; instead, the component of the frame 210" that is configured to connect the adjusting member 220", such as a snap slot or sliding track, etc., may be arranged in a slope form, so that the adjusting member 220" can also be slope in relation to the rotation plane of the frame 210". The adjusting member 220" has thickness difference in the direction perpendicular to the face of the patient, and the adjusting member 220" is sloped in relation to the rotation plane of the frame 210" as well as in relation to the reference plane. Utilizing the combined action of the arrangements, the supported height of the forehead support member 230 can be adjusted.

It should be noted that the adjustment scheme shown in FIGS. 9-10 can be combined with different embodiments described above. For example, the proximal surface of the adjusting member 220 shown in FIGS. 2-6 may be designed to be slope, and the adjusting member 220 may be adapted to be slope in relation to the rotation plane of the frame 210 (e.g., in relation to the reference plane). Similarly, the proximal surface of the adjusting member 220' shown in FIGS. 7-8 may be designed to be slope, and the adjusting member 220' may be adapted to be slope in relation to the plane of rotation of the frame 210 (e.g., in relation to the reference plane).

Though the adjusting members 220, 220' and 220" are in an annular shape respectively in the above embodiments, the adjusting members 220, 220', and 220" are not limited to that shape. They can be in any shape as long as they can be rotatably connected to the gas transfer interfaces 211 and 211". For example, the outer side wall of the adjusting member 220, 220' and 220" may be in a prism shape or frustum shape, and the inner side wall of the adjusting member may be essentially in a cylindrical shape, as long as the function of the adjusting member can be implemented. The outer side wall of the adjusting member 220, 220' and 220" may be provided with a plurality of teeth around the adjusting member, so that the adjusting member 220, 220' and 220" can be rotated by poking the adjusting member with a finger conveniently.

Embodiment 2

In embodiment 2 of the present application, the breathing mask provided in the present application can convert the rotation of an adjusting member into swing of a forehead support member by means of fitting between an adjusting track and a protrusion on the forehead support member and the adjusting member; thus, the height of a forehead support member in relation to the forehead of a patient can be adjusted by rotating the adjusting member.

Figure 11:
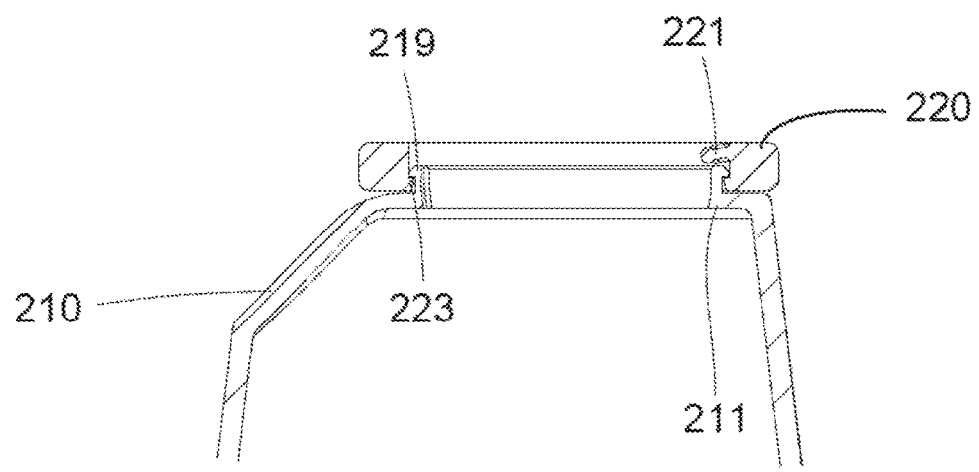
FIG. 11 is a sectional view of the adjusting member and the frame according to an embodiment of the present application.
Figure 12:
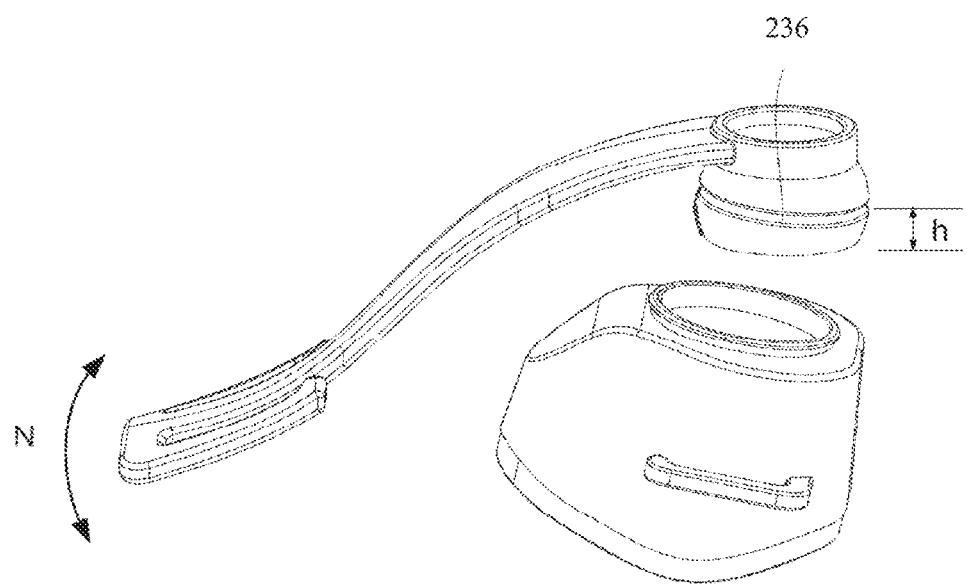
FIG. 12 is an exploded view of the forehead support member and the frame according to an embodiment of the present application.
Figure 13:
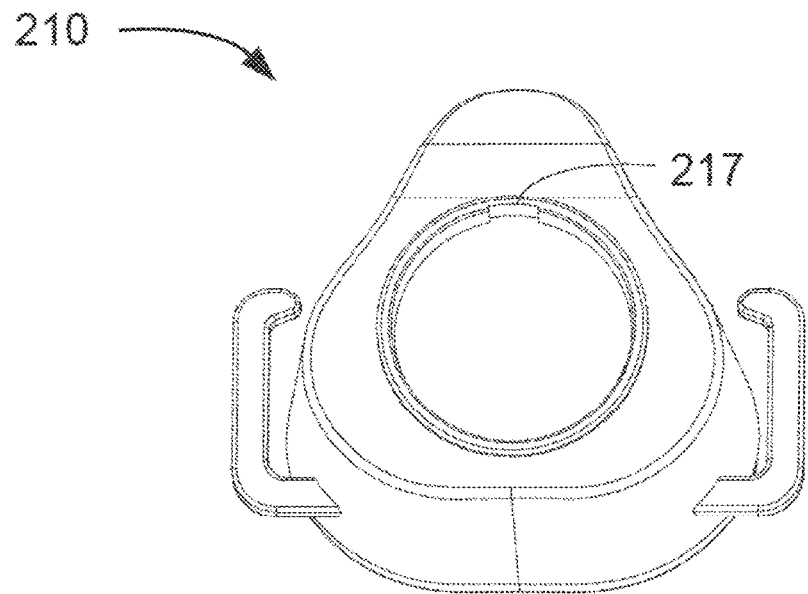
FIG. 13 is a 3D view of the frame according to an embodiment of the present application.
Figure 14:
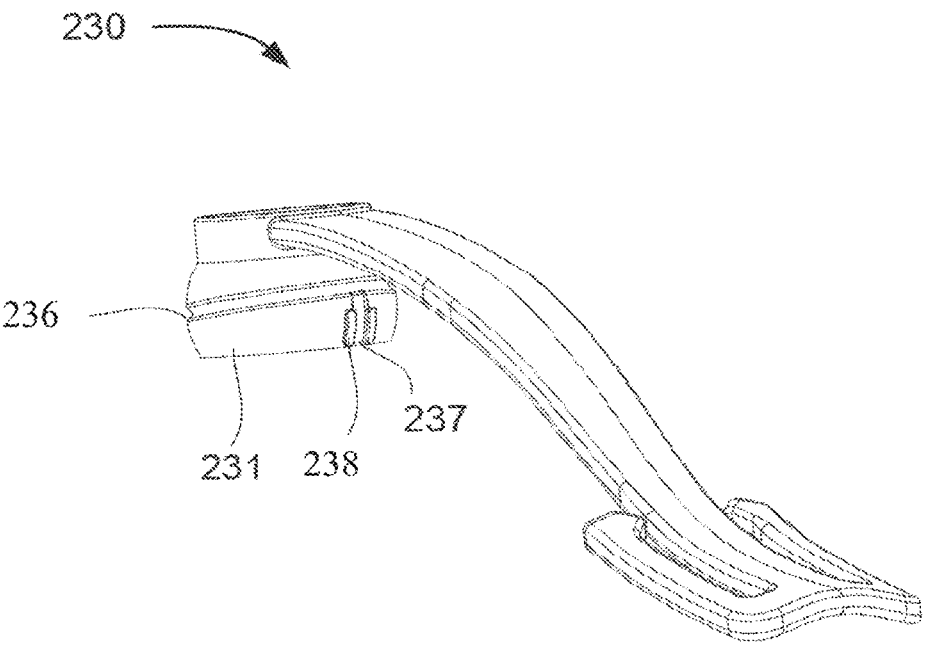
FIG. 14 is a 3D view of the forehead support member according to an embodiment of the present application.
Figure 15:
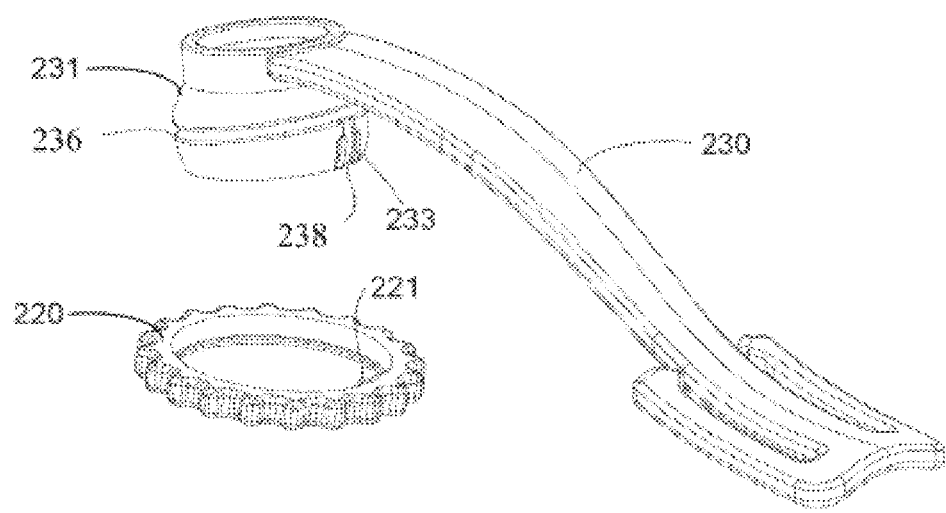
FIG. 15 is an exploded view of the forehead support member and adjusting member according to an embodiment of the present application.

FIGS. 11-15 show the components of the breathing mask 200 in embodiment 2 from different angles, wherein, FIG. 11 is a sectional view of the adjusting member and the frame according to an embodiment of the present application; FIG. 12 is an exploded view of the forehead support member and the frame according to an embodiment of the present application; FIG. 13 is a 3D view of the frame according to an embodiment of the present application; FIG. 14 is a 3D view of the forehead support member according to an embodiment of the present application; FIG. 15 is an exploded view of the forehead support member and adjusting member according to an embodiment of the present application.

Hereinafter the adjusting member 220 for adjusting the height of the forehead support pad in the embodiment 2 will be detailed. The adjusting member 220 is rotatably connected to the frame 210. Optionally, one of the adjusting member 220 and the frame 210 may be provided with a carrier, and the other of the adjusting member 220 and the frame 210 may be provided with a fitting component that move along the carrier, wherein, the above-mentioned carrier may comprise: a snap slot, which may form a snap-fit connection with the corresponding fitting component; or the above-mentioned carrier may comprise: a track, which may form a sliding connection with the corresponding fitting component.

In a preferred embodiment, as shown in FIG. 11, the adjusting member 220 is provided with a first snap slot 223, the frame 210 is provided with a second snap slot 219, and the first snap slot 223 and the second snap slot 219 can be snap-fitted with each other. The adjusting member is rotatably connected to the frame 210 via the first snap slot 223 and the second snap slot 219. The first snap slot 223 rotates in relation to the second snap slot 219, which make the adjusting member 220 can be rotated in relation to the frame 210. As an example, at least one of the first snap slot 223 and the second snap slot 219 is in an annular shape, so that the one of the first snap slot 223 and the second snap slot 219 may be rotated in relation to the other of the first snap slot 223 and the second snap slot 219. In an embodiment in which the adjusting member 220 is connected to the gas transfer interface 211, the first snap slot 223 and/or the second snap slot 219 may extend in the circumferential direction of the gas transfer interface 211, so that the adjusting member 220 can be rotated around the gas transfer interface 211. At least one of the first snap slot 223 and the second snap slot 219 may be an annular slot arranged continuously in the circumferential direction of at least one of them. Alternatively, the rotation of the adjusting member 220 and the frame 210 in relation to each other may be implemented with other fitting means. For example, one of the adjusting member 220 and the frame 210 may be provided with a circular track, and the other of the adjusting member 220 and the gas transfer interface 211 may be provided with any fitting part that slide along the circular track, such as a protrusion, a clamping hook, or teeth, etc.

Alternatively, the adjusting member 220 may be fitted over the first connecting part 231 of the forehead support member 230. Thus, the outer side wall of the first connecting part 231 and the inner side wall of the adjusting member 220 are opposite to each other at least partially. One of the outer side wall of the first connecting part 231 and the inner side wall of the adjusting member 220 is provided with a protrusion, and the other of the outer side wall of the first connecting part 231 and the inner side wall of the adjusting member 220 may be provided with an adjusting slope track. In an embodiment, the protrusion is arranged on the adjusting member 220, and the adjusting slope track is arranged on the forehead support member 230. In another embodiment, on the contrary, the protrusion is arranged on the forehead support member 230, and the adjusting slope track is arranged on the adjusting member 220. In terms of the adjustment of the height of the forehead support member in relation to the forehead, the principles of the two arrangements are essentially the same. Therefore, hereunder only one of the arrangements will be detailed with reference to the accompanying drawings. Those skilled in the art can understand the other arrangement on the basis of the following description.

The inner side wall of the adjusting member 220 is provided with a protrusion 221, as shown in FIGS. 11 and 15. The outer side wall of the first connecting part 231 is provided with an adjusting slope track 236, as shown in FIGS. 12, 14 and 15. The adjusting slope track 236 surrounds the first connecting part 231. The adjusting slope track 236 is generally in an annular shape. The protrusion 221 can slide along the adjusting slope track 236. As an example, the protrusion 221 may be a ball that protrudes from the inner side wall of the adjusting member 220. The ball may be received in the adjusting slope track 236 so that it can slide along the adjusting slope track 236. The protrusion 221 may be in any other construction, as long as it can slide along the adjusting slope track 236. The adjusting slope track 236 is slope in relation to a reference plane. The reference plane mentioned here is a vertical plane parallel to the pivot shaft O-O. The reference plane is an imaginary plane, and is not shown in the drawings; however, with reference to FIG. 4, it can be understood that the reference plane is a vertical plane perpendicular to the paper surface. When a patient wears the breathing mask, the reference plane is parallel to the face of the patient. As shown in FIG. 12, the height h of the adjusting slope track 236 in relation to the proximal end of the first connecting part 231 varies gradually in the circumferential direction of the first connecting part 231. Thus, when the adjusting member 220 is rotated, the protrusion 221 may slide to different positions in the adjusting slope track 236 and thereby drive the forehead support member 230 to swing (i.e., swing in the direction indicated by the arrow N); accordingly, the height of the forehead support member 230 in relation to the forehead is adjusted. Thus, the patient can find out the most comfortable position simply according to his/her feeling by rotating the adjusting member 220 with a single hand, without any help from any other person. The slope angle of the adjusting slope track 236 in relation to the reference plane may be designed according to the desired height adjustment range of the forehead support member 230. Thus it is seen: the adjusting member 220 is designed skillfully to implement height adjustment of the forehead support member 230, and is simple in structure and manufacturing. Therefore, the cost can be saved.

In the case of a ball and socket connection, to limit the swing direction of the forehead support member 230 (e.g., forcing the forehead support member 230 to pivot around the pivot shaft O-O, which serves as an axis), the forehead support member 230 and the frame 210 are respectively provided with a limit part, and the two limit parts are fitted with each other. Please see FIG. 13 that shows the frame 210 and FIG. 14 that shows the forehead support member 230. The limit part 233 on the forehead support member 230 is a limit protrusion, and the limit part 217 on the frame 210 is a limit slot. The position of the limit protrusion 238 is provided correspondingly to the position of the limit slot 217. The limit protrusion 238 slides along the limit slot 217 when the forehead support member 230 is pivoted. The limit parts may be implemented in other ways, for example, the positions of the limit protrusion and the limit slot on the forehead support member 230 and the frame 210 may be exchanged, or flat faces (may be perpendicular to the pivot shaft O-O) that match each other may be arranged on the forehead support member 230 and the frame 210, etc. With the limit parts, though the forehead support member 230 and the frame 210 are connected via a ball and socket connection, there is only one degree of freedom of adjustment in the height direction of forehead. However, as described below, the outer side wall of the first connecting part 231 of the forehead support member 230 or the inner side wall of the adjusting member 220 is arranged with an adjusting slope track that extends in the circumferential direction of the respective component. Therefore, the design difficulty will be increased if flat faces that match each other are used to restrict the forehead support member 230 to pivot around the pivot shaft O-O only. However, the present application doesn't exclude such an arrangement. The fitting scheme of the limit protrusion 238 and the limit slot 217 makes the structure of the limit parts relatively simple.

Preferably, the adjusting member 220 is detachably connected to the forehead support member 230. The forehead support member 230 and the frame 210 may also be connected detachably. In view that the breathing mask has to be cleaned frequently, the components of the breathing mask can be disassembled with such detachable connections; therefore, such detachable connections are very helpful for the cleaning work. In a preferred embodiment of the present application, in the outer side wall of the first connecting part 231 and the inner side wall of the adjusting member 220, the side wall where the adjusting slope track is arranged is provided with a slot. For example, in the embodiment shown in FIG. 15, the outer side wall of the first connecting part 231 of the forehead support member 230 is provided with an adjusting slope track 236 and a slot 237. The slot 237 has a first end and a second end. The first end of the slot 237 is connected to the adjusting slope track 236. The second end of the slot 237 extends to an edge of the outer side wall. Since the adjusting slope track 236 communicates with the slot 237, the protrusion 221 may slide along the slot 237 into the adjusting slope track 236 or disengage from the slot 237 from the second end of the slot 237, so that the adjusting member 220 can be removed from the forehead support member 230. With the slot 237, the adjusting member 220 can be disassembled from the forehead support member 230 conveniently, and the adjusting member 220 can be mounted simply by aligning the protrusion 221 to the slot 237 and then sliding the protrusion 221 into the adjusting slope track 236. The embodiment in which the adjusting slope track is arranged on the adjusting member 220 is similar to the above embodiment, i.e., the slot is arranged on the inner side wall of the adjusting member 220 and connected to the adjusting slope track. For brevity, that embodiment will not be detailed further here.

Optionally, in the illustrated embodiment, the slot 237 is perpendicular to the adjusting slope track 236. However, the slot 237 may not be perpendicular to the adjusting slope track 236 alternatively. The slot 237 may be at an angle from the adjusting slope track 236. Though the structure will be slightly more complex in the embodiment in which the slot 237 is not arranged perpendicularly when compared with the embodiment in which the slot 237 is arranged perpendicular to the adjusting slope track 236, in return, the non-perpendicular arrangement can decrease the probability that the protrusion 221 disengages from the slot 237 accidentally. Further preferably, the limit parts mentioned above may comprise a limit protrusion arranged on the outer side wall of the first connecting part 231 and a limit slot arranged on the frame 210 correspondingly to the limit protrusion. The fitting scheme of limit protrusion and limit slot has been described in detail above, and will not be further detailed here. It is worthy to note: in the embodiment in which the adjusting slope track 236 and the slot 237 are arranged on the outer side wall of the first connecting part 231 of the forehead support member 230, the limit protrusion 238 preferably is arranged at the two sides of the slot 237, as shown better in FIGS. 14-15. In consideration of wearing comfortability, breathing masks are designed to be smaller and smaller. For the limited wall thickness of the first connecting part 231, the depth of the slot 237 can be increased by arranging the limit protrusion 238 at two sides of the slot 237. Thus, in the process that the adjusting member 220 is mounted to the forehead support member 230 or removed from the forehead support member 230, the protrusion 221 can be aligned to the slot 237 more easily; therefore, the mounting and removal are more convenient and quicker.

Though the adjusting members 220 in the above embodiments are in an annular shape respectively, the adjusting members 220 are not limited to that shape. They can be in any shape as long as they can be rotatably connected to the gas transfer interface 211. For example, the outer side wall of the adjusting member 220 may be in a prism shape or frustum shape, and the inner side wall of the adjusting member may be essentially in a cylindrical shape, as long as the function of the adjusting member can be implemented. The outer side wall of the adjusting member 220 may be provided with a plurality of teeth around the adjusting member, so that the adjusting member 220 can be rotated by poking the adjusting member with a finger conveniently.

While the present application is described above in embodiments, it should be appreciated that the above embodiments are provided only for an illustration and description purpose rather than intended to limit the present application to the scope defined by the embodiments. Those skilled in the art should appreciate that the present application is not limited to the above-mentioned embodiments. More variations and modifications can be made on the basis of the teaching provided in the present application, and those variations and modification shall be deemed as falling in the claimed scope of protection of the present application. The scope of protection of the present application is only defined by the attached claims and their equivalents.

The invention claimed is:

1. A breathing mask, comprising:
   a frame provided with a gas transfer interface, which has a central axis;
   a forehead support member, which has a first connecting part pivotally connected to the frame to allow the forehead support member to swing toward the forehead of a patient or away from the forehead of the patient; and
   an adjusting member, which is rotatably connected to the frame and surrounds the gas transfer interface, and is fitted over the first connecting part;
   wherein, the forehead support member is driven to swing by means of the rotation of the adjusting member about the central axis of the gas transfer interface,
   wherein, the first connecting part of the forehead support member has an outer side wall, the adjusting member has an inner side wall, one of the outer side wall and the inner side wall is provided with a protrusion, the other is provided with a adjusting slope track, and the protrusion may slide along the adjusting slope track.

2. The breathing mask according to claim 1, wherein the outer side wall or the inner side wall in which the adjusting slope track is arranged is provided with a slot, which has a first end connected to the adjusting slope track and a second end extending to an edge of the outer side wall or the inner side wall in which the adjusting slope track is arranged, and the protrusion may slide along the slot and may disengage from the slot from the second end.

3. The breathing mask according to claim 2, wherein the adjusting slope track is arranged on the outer side wall of the first connecting part, the outer side wall is provided with a limit protrusion, the frame is correspondingly provided with a limit slot, and the limit protrusion is fitted with the limit slot to limit the swing direction of the forehead support member.

4. The breathing mask according to claim 3, wherein the limit protrusion is arranged at two sides of the slot.

5. The breathing mask according to claim 2, wherein the slot is perpendicular to the adjusting slope track.

6. The breathing mask according to claim 1, wherein one of the adjusting member and the frame is provided with a carrier, and the other of the adjusting member and the frame is provided with a fitting component that move along the carrier.

7. The breathing mask according to claim 1, wherein the forehead support member has a first connecting part, the frame has a second connecting part, the first connecting part and the second connecting part are fitted with each other to form a ball and socket connection structure, the forehead support member and the frame are respectively provided with a limit part fitted with each other to limit the swing direction of the forehead support member.

8. The breathing mask according to claim 1, wherein the outer side wall of the adjusting member is provided with a plurality of teeth arranged around the adjusting member.

* * * * *